United States Patent
Lowe et al.

(10) Patent No.: US 11,020,491 B2
(45) Date of Patent: Jun. 1, 2021

(54) IN VIVO RADICAL-MEDIATED POLYMERIZATION FOR TARGETED DELIVERY OF TROPHIC FACTORS

(71) Applicant: Rutgers, The State University of New Jersey, New Brunswick, NJ (US)

(72) Inventors: Christopher Lowe, Piscataway, NJ (US); David I. Shreiber, Whitehouse Station, NJ (US); Emily DiMartini, Piscataway, NJ (US); Adam Gormley, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/009,033

(22) Filed: Jun. 14, 2018

(65) Prior Publication Data

US 2018/0360989 A1    Dec. 20, 2018

Related U.S. Application Data

(60) Provisional application No. 62/519,465, filed on Jun. 14, 2017.

(51) Int. Cl.
| | |
|---|---|
| *A61K 47/10* | (2017.01) |
| *A61K 47/32* | (2006.01) |
| *A61K 47/34* | (2017.01) |
| *A61K 47/69* | (2017.01) |
| *C08L 33/06* | (2006.01) |
| *C08L 33/26* | (2006.01) |
| *C08L 33/20* | (2006.01) |

(52) U.S. Cl.
CPC .......... *A61K 47/6935* (2017.08); *A61K 47/10* (2013.01); *A61K 47/34* (2013.01); *C08L 33/06* (2013.01); *A61K 47/32* (2013.01); *C08L 33/20* (2013.01); *C08L 33/26* (2013.01); *C08L 2203/02* (2013.01)

(58) Field of Classification Search
None
See application file for complete search history.

(56) References Cited

U.S. PATENT DOCUMENTS

| | | | | |
|---|---|---|---|---|
| 5,994,341 A | * | 11/1999 | Hunter | A61K 9/1635 514/250 |
| 8,217,166 B2 | | 7/2012 | Salvemini et al. | |
| 2003/0220245 A1 | * | 11/2003 | Hubbell | A61K 31/337 525/50 |

(Continued)

OTHER PUBLICATIONS

West, et al: "Polymeric Biomaterials with Degradation Sites for Proteases Involved in Cell Migration", Macromulecules, 1999, vol. 32, No. 1, pp. 241-244.

(Continued)

*Primary Examiner* — Brian Gulledge
(74) *Attorney, Agent, or Firm* — Fox Rothschild LLP

(57) ABSTRACT

The present invention provides a biocompatible conjugate for treating a disease or an injury. The conjugate contains a polymer covalently linked to one or more moieties each containing a polymerizable functional group. The conjugate forms a cross-linked polymer network after being exposed to an elevated level of free radicals associated with the disease or injury.

23 Claims, 8 Drawing Sheets

(56) References Cited

U.S. PATENT DOCUMENTS

2004/0234573 A1* 11/2004 Mollison ................ A61L 27/34
424/423

OTHER PUBLICATIONS

Liu, et al: "Polyethylene Glycol-Conjugated Superoxide Dismutase and Catalase Reduce Ischemic Brain Injury", American Journal of Physiology—Heart and Circulatory Physiology, 1989, No. 256, pp. H589-H593.

Luo, et al: "Polyethylene Glycol Immediately Repairs Neuronal Membranes and Inhibits Free Radical Production after Acute Spinal Cord Injury", Journal of Neurochemistry, 2002, vol. 83, pp. 471-480.

Russell, et al: "Poly(ethylene glycol) Hydrogel-Encapsulated Fluorophore-Enzyme Conjugates for Direct Detection of Organophosphorus Neurotoxins", Analytical Chemistry. Nov. 1, 1999, vol. 71, No. 21, pp. 4909-4912.

Zhang et al: "Conjugated of Brain-Derived Neurotrophic Factor to a Blood-Brain Barrier Drug Targeting System Enables Neuroprotection in Regional Brain Ischemia Following Intravenous Injection of the Neurotrophin", Brain Research, 2001, vol. 889, pp. 49-56.

Lee, et al: "Poly(ethylene glycol) Hydrogels Conjugated with a Collagenase-Sensitive Fluorogenic Substrate to Visualize Collagenase Activity During Three-Dimensional Cell Migration", Biomaterials, 2007, vol. 28, pp. 3163-3170.

* cited by examiner

IN VIVO RADICAL-MEDIATED POLYMERIZATION FOR TARGETED DELIVERY OF TROPHIC FACTORS

CROSS-REFERENCE TO RELATED APPLICATIONS

This application claims the benefit of U.S. Provisional Application Ser. No. 62/519,465, filed Jun. 14, 2017, which is hereby incorporated by reference.

STATEMENT REGARDING FEDERALLY FUNDED RESEARCH

This invention was made in part with government support under Grant No. NSF EEC 1262924 awarded by the National Science Foundation. The government has certain rights in the invention.

FIELD OF THE INVENTION

The present invention relates to injury repair and wound healing by utilizing the radicals or stimuli generated during the injury to mediating the polymerization of a functionalized biomaterial. In particular, this strategy mitigates the damage to cells after an injury and promote faster healing.

BACKGROUND OF THE INVENTION

Targeted drug delivery offers the promise to selectively and precisely deliver drug payloads directly to the cells and tissues that require the therapeutic, which can minimize required dosages and off-target side effects. Successful targeted drug delivery requires a balance of specificity and sensitivity. Various types of drug-carrying nanoparticles have been developed to carry a therapeutic agent to the target tissue following systemic delivery. Here, target-specific ligands are coupled to the nanoparticle surface to selectively bind to a single cell surface receptor. In cancer treatment, receptors overexpressed on the tumor cell's surface are identified as substrates for ligand-receptor interactions. This approach, however, requires the identification of ligands that are unique to cell surface receptors on different types of tumors. As such, new targets and ligands must be identified for any new application, which is both non-trivial and costly. Further, tumors do not evenly express surface cell receptors throughout the tumor mass, and the expressed receptors continuously change. The heterogeneity within tumors and between tumor types limits the therapeutic capabilities of a ligand-based targeting approach. Additionally, receptors that are overexpressed in tumor cells are also expressed to a lesser degree in healthy cells, which can lead to off-target dumping.

An example of a condition in need of an effective treatment is Traumatic Brain Injury (TBI). TBI is a leading cause of death and disability worldwide, most often resulting from motor vehicle crashes, falls, violence, and sports injuries. It is estimated that between 12,000 and 15,000 new cases of TBI occur each year in New Jersey alone, and an estimated 2.6 million emergency department visits, hospitalizations and deaths each year are the result of TBI across the United States. The effects of TBI vary greatly in terms of the severity of the injury and the region of the brain that is afflicted, however those affected with TBI often face prolonged disability stemming from functional and cognitive deficits, greatly reducing overall quality of life. Unfortunately, the central nervous system has a limited capacity for self-repair, and there currently exist no fully restorative interventions or treatments to combat the effects of TBI. These injuries are estimated to represent an economic burden of more than $60 billion annual in direct medical costs and costs resulting from lost productivity of those afflicted. TBI most often presents in young adult patients, exacerbating the economic costs and reduced quality of life throughout their lifetime.

TBI presents in a variety of ways, most often by severe contusion, which results in damage to neurons and glia. This initial insult, referred to as the primary injury, occurs instantaneous with the trauma. A prolonged, inflammatory injury cascade follows the primary injury, resulting in altered levels of neurotransmitters, activation of microglia, and the formation of a glial scar. Collectively these complicated effects are referred to as secondary injury, and their onset begins a feedback cycle, where these co-morbidities perpetuate one another, causing secondary injury to persist long after the primary injury. Specifically, neurons in the injured area undergo widespread depolarization. Levels of neurotransmitters spike, particularly glutamate, which typically induces excitotoxicity. The prolonged inflammatory environment causes an accumulation of activated microglia, reactive astrocytes, and basal membrane, forming a glial scar. The glial scar represents a physical barrier to regeneration, but these cells also secrete a variety of inhibitory factors resulting in a hostile chemical environment at the injury site.

A key component of secondary injury is the generation of free-radicals. Free-radicals are molecules left with at least one unpaired electron and are extremely reactive, capable of causing significant damage to proteins, lipid membranes, and nucleic acids. Following TBI, levels of both reactive oxygen species (ROS) and reactive nitrogen species (RNS) are increased. Increased production of superoxide radical, $O_2\cdot^-$, and hydroxyl radical, $\cdot OH$, is observed shortly after injury, most often resulting from mitochondrial damage and dysfunction, but elevated levels persist at longer time points generated by activated microglia. The primary RNS, $NO\cdot$, is a critical chemical messenger in a variety of native pathways. TBI induces the activation of nitric oxide synthase, which results in increased levels of NO. in the post traumatic brain. The presence of these radicals can initiate lipid peroxidation, as radicals reacting with lipid molecules steal an electron to form lipid radical. These lipid radicals then oxidize neighboring lipids, propagating a chain reaction that destabilizes membranes throughout the cell, including further damage to mitochondria, which increases the production of radicals. Further, $NO\cdot$ and $O_2\cdot^-$ can combine to form perioxinitrate, $ONOO^-$. While not a radical itself, $ONOO^-$ can still oxidize lipids to induce lipid peroxidation, as well as damage proteins, and nucleic acids, making it equally as formidable as its radical precursors. Cells do have means of reducing or eliminating excess free radicals to maintain an optimal homeostatic environment. In the post traumatic brain. However, in the post traumatic brain, these native mechanisms are quickly overwhelmed and insufficient to prevent significant radical damage.

A need exists to develop novel biomaterial strategies to target therapeutics to regions of damaged or diseased tissues.

SUMMARY OF THE INVENTION

A potential candidate for targeting a broader array of disorders are free radicals. Elevated concentrations of free radicals are characteristic of a wide variety of tissue injuries and disease states, such as inflammatory diseases, neurological disorders, ischemic diseases, burn wounds, cancer, radiation exposure, organ transplantation, and traumatic brain injuries.

The present invention provides an approach that does not have to target cells but rather a species that is produced under pathologic situations and allows for targeted delivery to be applied to a broader range of injury and disease conditions. For instance, a multi-potent conjugate of the present invention can (1) react with free radicals to protect tissue and (2) form higher molecular weight species that is immobilized in the injury site, thereby (3) localizing the delivery and sustaining the presentation of a therapeutic bound to the conjugate.

An aspect of the invention relates to a biocompatible conjugate comprising a polymer covalently linked to one or more moieties each containing an addition reaction functional group. Through intermolecular reactions between the functional groups, the conjugate polymerizes to form a cross-linked polymer network after being exposed to an abnormal level of free radicals associated with the disease or injury. In some embodiment, the polymer and/or any moiety of the conjugate are linked to a therapeutic agent or diagnostic agent. In some embodiments, the polymer and/or the one or more moieties of the conjugate comprise a degradable linkage. The degradation of the linkage promotes the clearance of the conjugate from the blood circulation or the release of a therapeutic agent or diagnostic agent. In some embodiments, the polymerizable functional groups are independently alkene, alkyne or thiol.

The polymer can be synthetic or natural in origin. In some embodiments, the polymer has a molecular weight ranging from about 1,000 Dalton to about 30,000 Dalton. In some embodiments, the polymer is a synthetic polymer selected from the group consisting of polymeric polyol, poly(lactic acid) (PLLA), poly(lactic-co-glycolic acid) (PLGA), Poly (caprolactone), Poly(vinyl alcohol), Polyurethenes, Polyamides and Poly(2-hydroxyethyl methacrylate) (Poly (HEMA)). In some embodiments, the polymer is a natural polymer selected from the group consisting of Chitosan, Collagen, Gelatin, Hyaluronic Acid, Chondroitin Sulfates, Fibrin, Alginate, Agarose and Cellulose. In some embodiments, the polymer is selected from the group consisting of polyether, polyester, polyethylene, polyethylene glycol, polypropylene glycol, and polybutylene glycol polyols. A preferred polymer is polyethylene glycol (PEG).

The moieties bonded to the polymer are each independently selected from the group consisting of acrylate, acrylamide, (metha)acrylate, (metha) acrylamide, acrylonitrile, a thiol-containing moiety, and an alkyne-containing moiety. In some embodiments, the moieties are each independently acrylate or (metha)acrylate. In some embodiments, the acrylate is substituted. Various alkenes, therapeutic agents, and targeting agents can be attached to the polymer or the functional group-containing moieties. In some embodiments, the therapeutic agents are selected from the group consisting of neurotrophic factors, growth factors, cytokines, biologics, anti-inflammatory drugs, antibiotics and antimicrobial peptides and angiogenic factors. In some embodiments, the therapeutic agents are neurotrophic factors selected from Brain-derived neurotrophic factor (BDNF), Ciliary neurotrophic factor (CNTF), Nerve growth factor (NGF), Glial cell-derived neurotrophic factor (GDNF) and Glia maturation factor (GMF).

The conjugate may further comprise a hydrolytically, enzymatically, or photonically degradable linkage. A degradable linkage may also be incorporated to the conjugate to control the clearance and the release of the payload drug. In some embodiments, the degradable linkage links a therapeutic agent to the conjugate. In some embodiments, the clearance of the polymer network is initiated by the degrading of the degradable linkage.

In some embodiments, the degradable linkage contains a group selected from the group consisting of an ester, an amide, a hydrazone, a carbamate, a disulfide, an oxime, a semicarbazide, a carbodiimide, an acid labile group, photo-labile group, peptidase labile group and esterase labile group.

Another aspect provides a pharmaceutical composition comprising the conjugate of the invention and a pharmaceutically acceptable carrier. In some embodiments, the composition contains a plurality of conjugates characterized by both natural and synthetic polymers.

Another aspect provides a kit for treating a disease or an injury characterized by an abnormal production of free radicals, comprising a first conjugate and second conjugate, wherein the first conjugate comprises a linear or multi-arm polymer covalently linked to a first cycloaddition functional group and a moiety containing a polymerizable functional group, wherein a cross-linked polymer network is formed through intermolecular reactions between the polymerizable functional groups after being exposed to an abnormal level of free radicals associated with a disease or injury; the second conjugate comprises a linear or multi-arm polymer covalently linked to a second cycloaddition functional group and a therapeutic agent or diagnostic agent; and the first cycloaddition functional group and the second cycloaddition functional group form a ring through click chemistry. In some embodiments, the first cycloaddition functional group and the second cycloaddition functional group are selected from the group consisting of dibenzocyclooctyl (DBCO), azide, trans-cyclooctene and tetrazine.

Also provided is a method of treating a disease or injury associated with an elevated level of free radicals with the conjugate or kit of the invention. In addition to initiating crosslinking, the reaction of free radicals with the functional group of the conjugate may sequester or otherwise occupy the free radicals to prevent damage to nearby cells and offer a measure of cellular protection. The disease or injury may include for example traumatic brain injury, burn injury, inflammatory disease, bacterial infection, neurological disorder and ischemic disease. The method is also applicable to procedures or conditions such as organ transplantation, ulcers, and radiation.

In some embodiments, the injury is a skin wound associated with a higher than normal level of free radicals near the wound site. In some embodiments, the conjugate further comprises a therapeutic agent. In some embodiments, the therapeutic agent is an anti-cancer agent and the conjugate is immobilized at the site of a tumor.

DETAILED DESCRIPTION OF THE INVENTION

Figure 1:
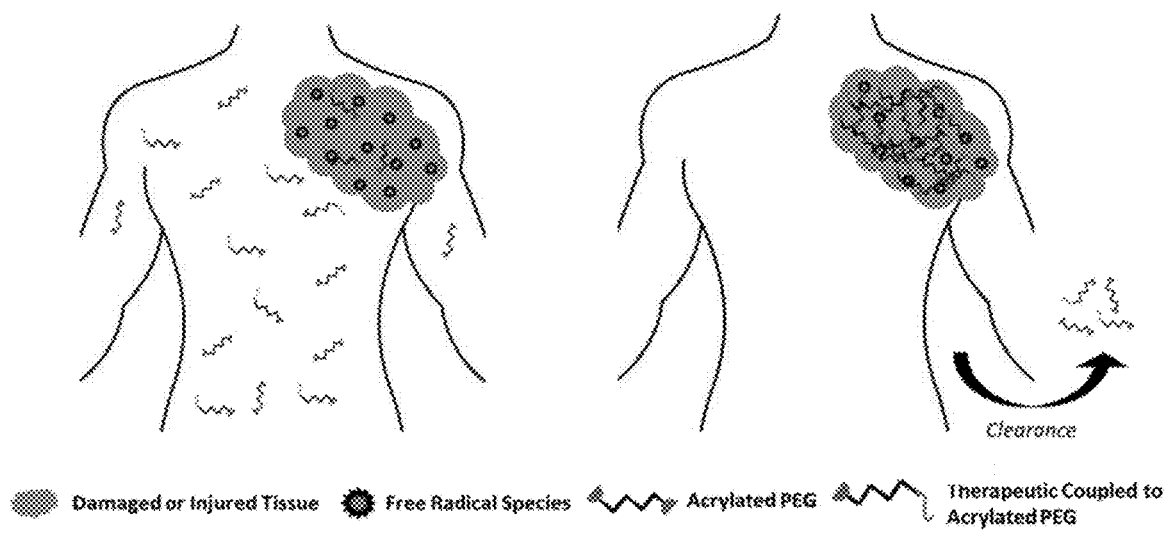
FIG. 1 illustrates the accumulation of therapeutic-functionalized acrylated PEG. A mixture of acrylated PEG and acrylated PEG functionalized with therapeutic is introduced to the body following injury or disease. Free radicals at the injury site react with the acrylate groups to induce cross-linking, which immobilizes the therapeutic at the site of highest radical concentration. PEG that is not polymerized or crosslinked is cleared.
Figure 2:
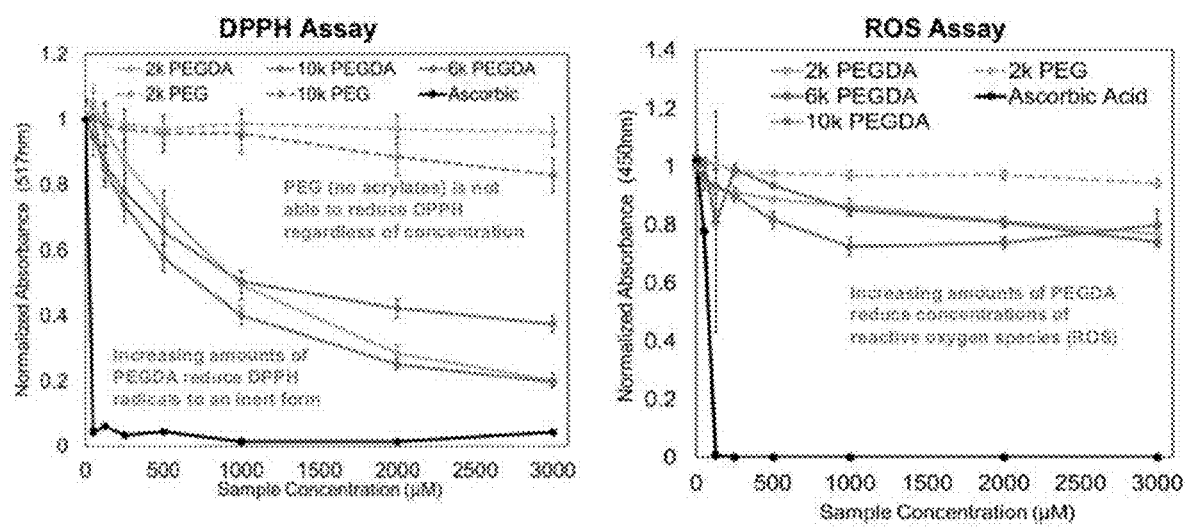
FIG. 2 illustrates the reduction of radicals by acrylated in DPPH assay and ROS assay.
Figure 3:
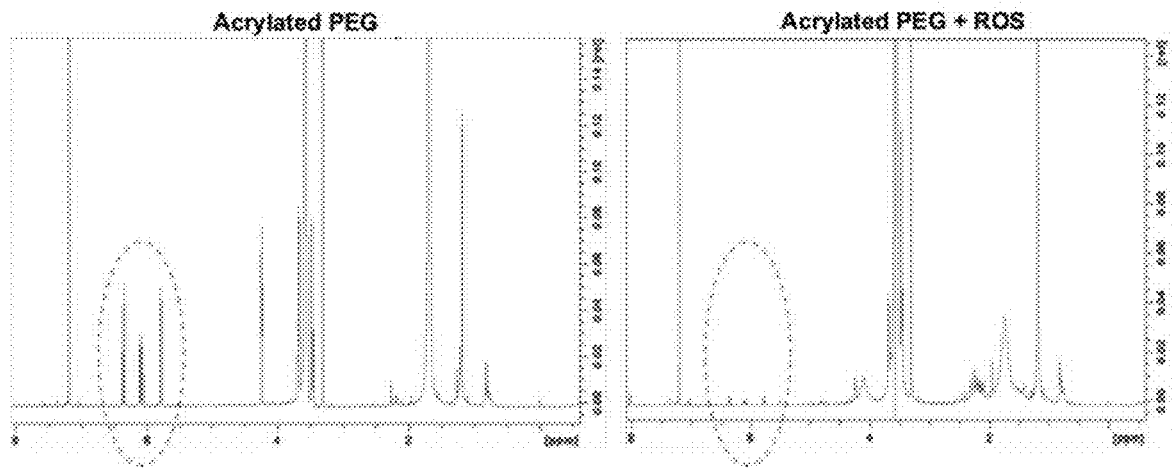
FIG. 3 illustrates the reduction of acrylate NMR signal after reaction with ROS derived free radicals.
Figure 4:
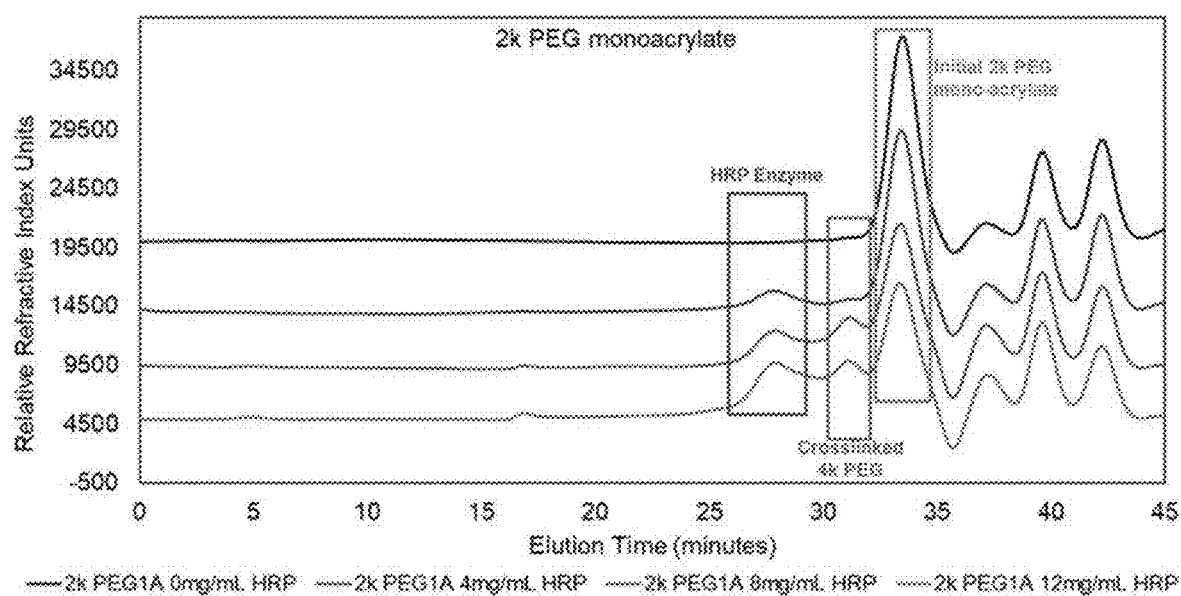
FIG. 4 illustrates the gel permeation chromatography after cross-linking of acrylated PEGs.
Figure 5:
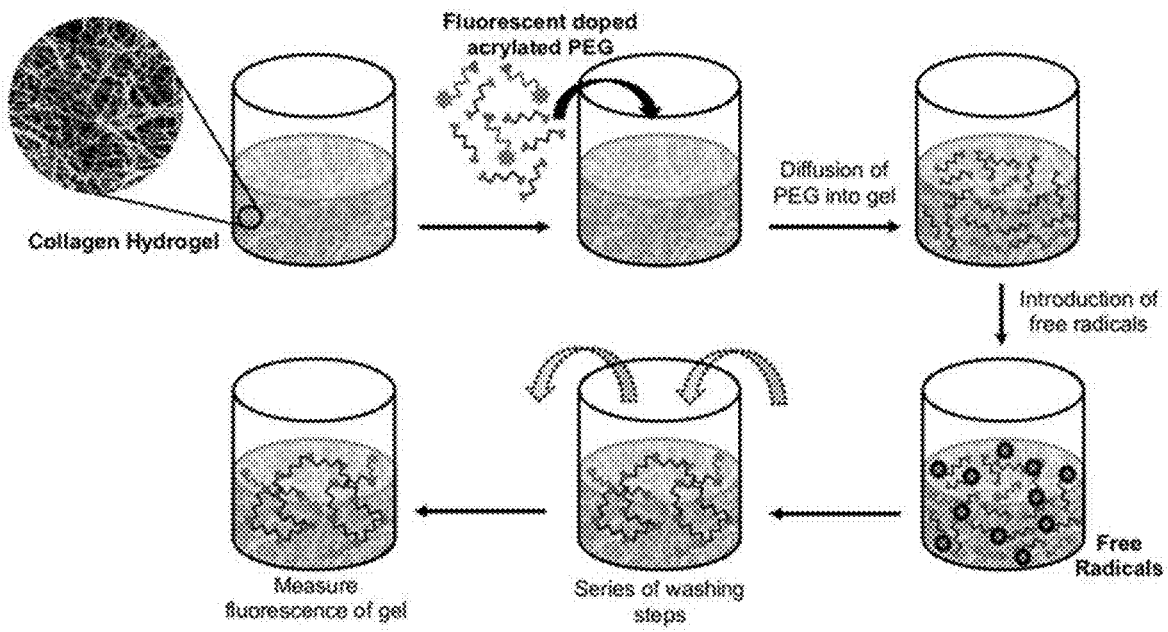
FIG. 5 illustrates the immobilization of acrylated PEGs in tissue mimics.
Figure 6:
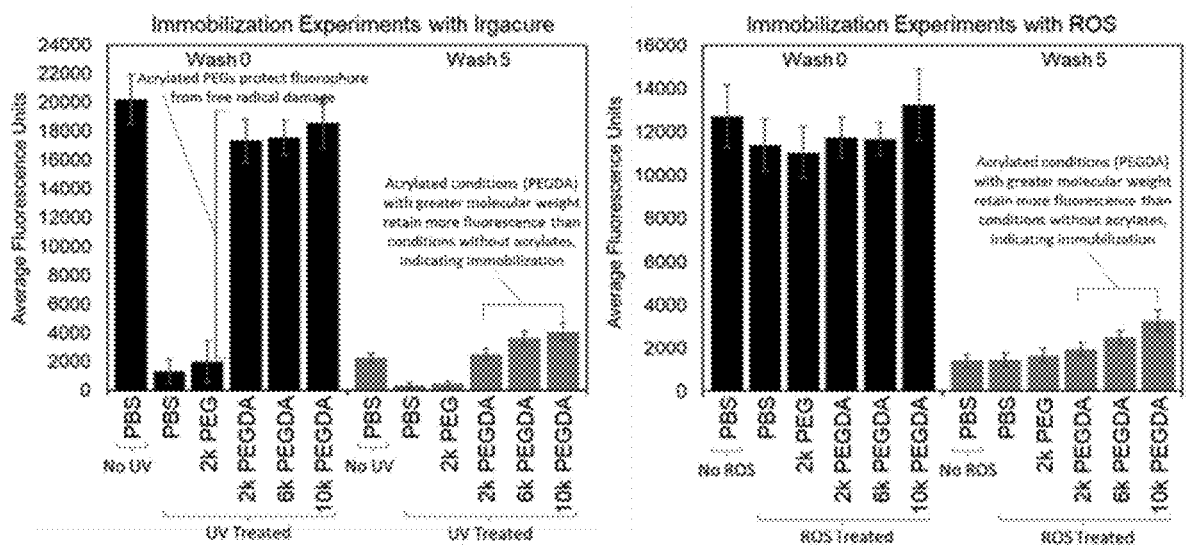
FIG. 6 illustrates immobilization of PEGDA in comparison with non-functionalized PEG and PBS controls.
Figure 7:
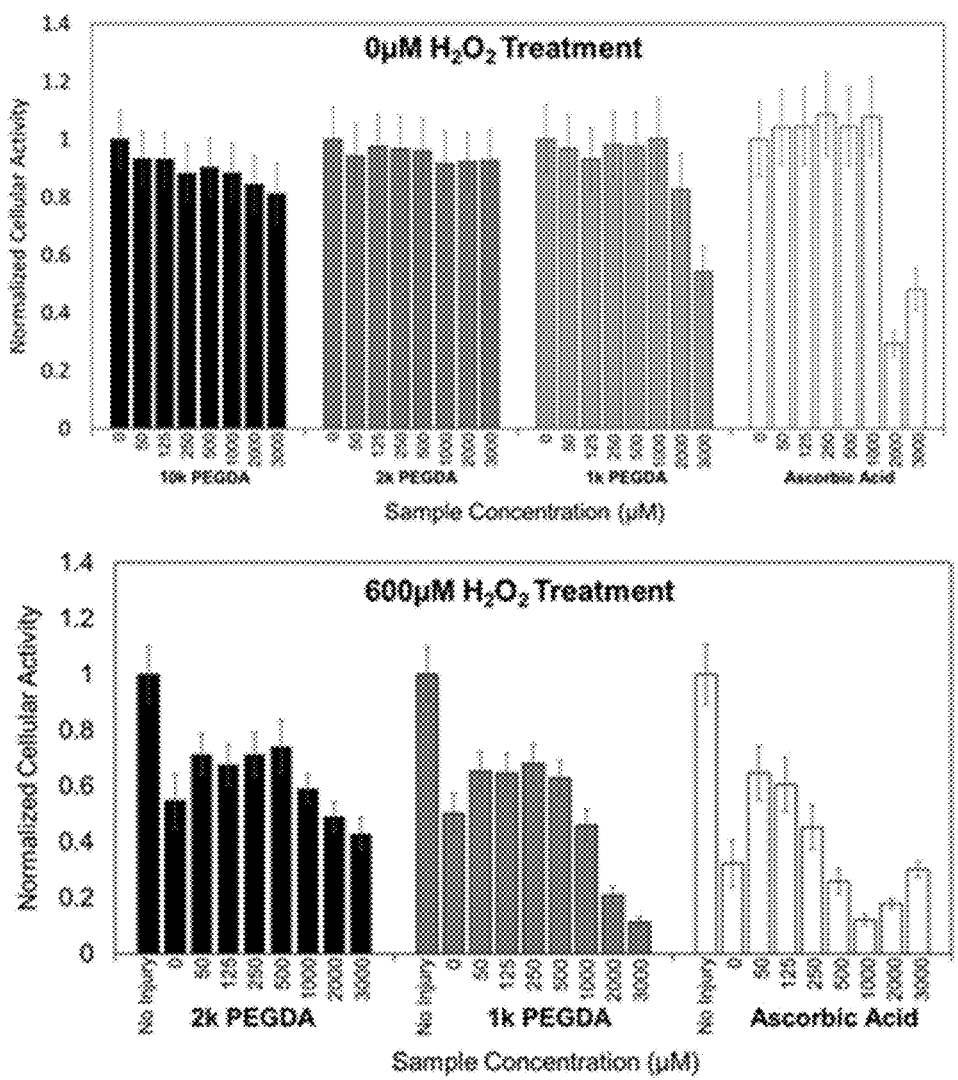
FIG. 7 illustrates the cellular activity in the presence and absence of acrylated PEG when exposed to free radicals.
Figure 8:
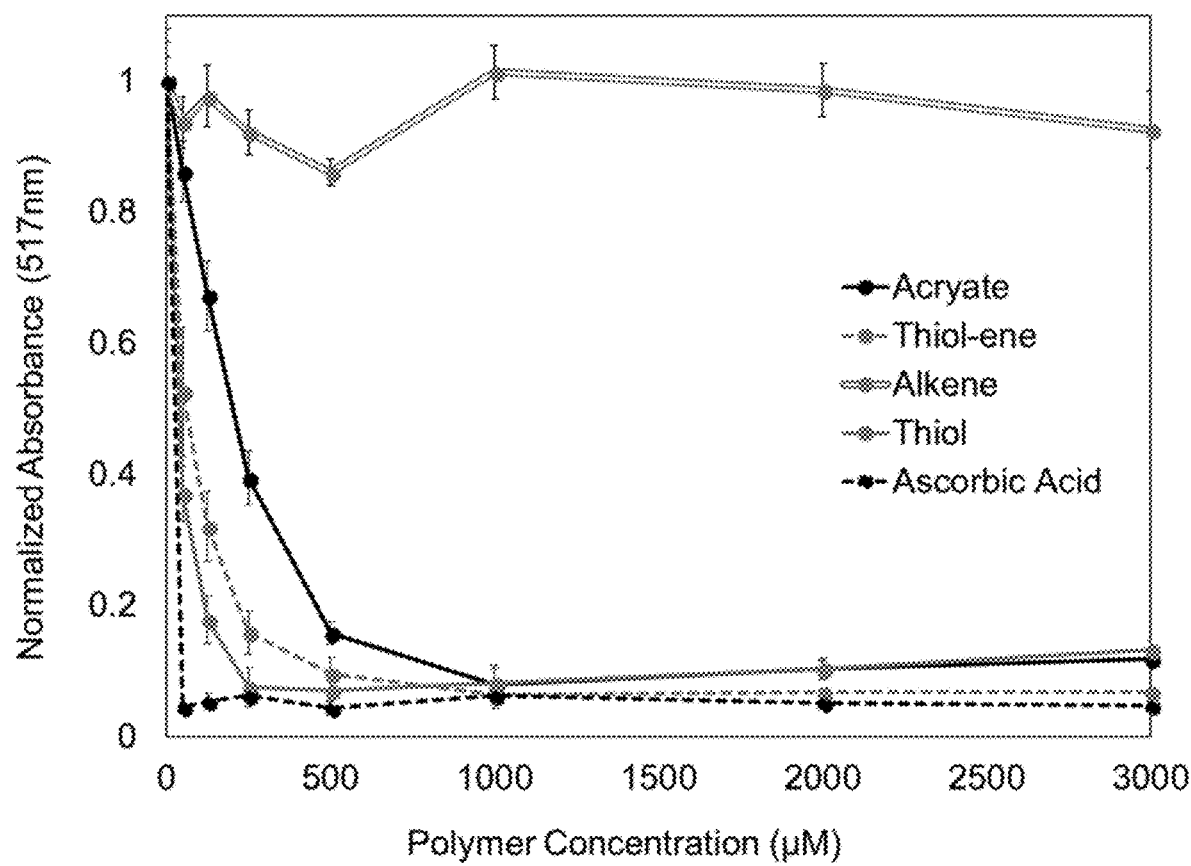
FIG. 8 illustrates the reduction of DPPH radicals by thiol, alkene, acrylate, and thiol-ene functional groups attached to PEG compared to ascorbic acid.
Figure 9:
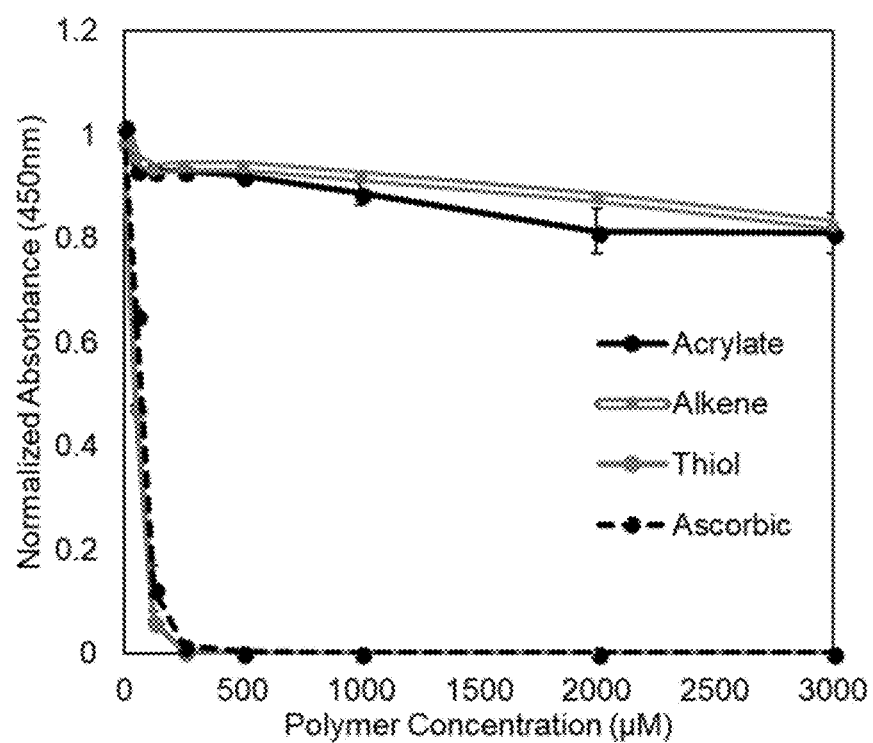
FIG. 9 illustrates the reduction of ROS radicals by thiol, alkene, and acrylate functional groups attached to PEG compared to ascorbic acid.
Figure 10:
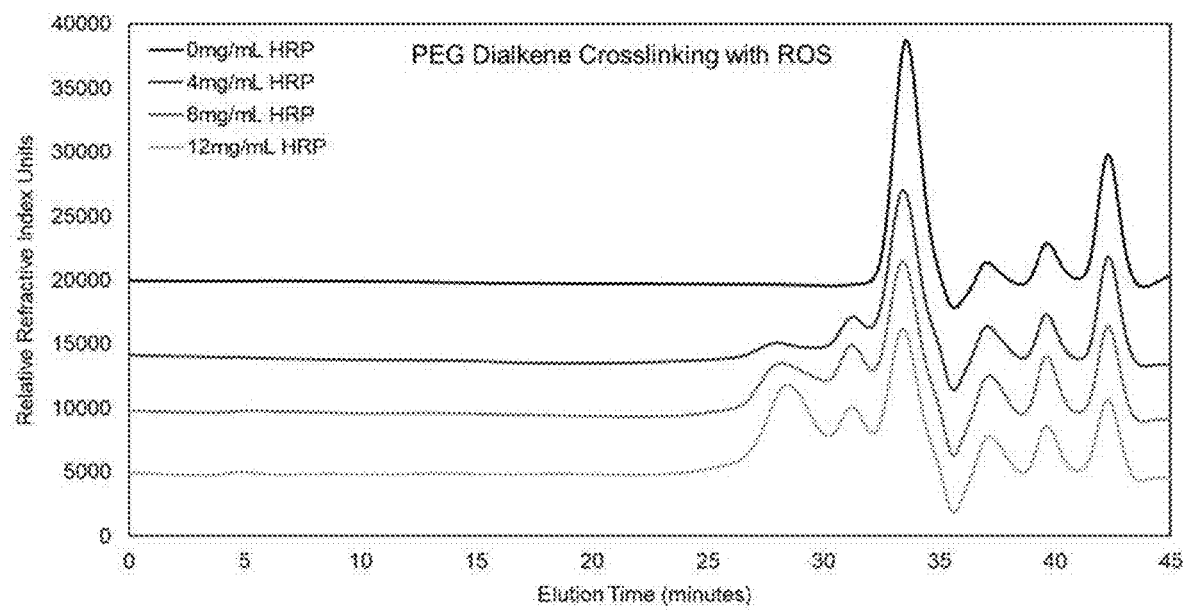
FIG. 10 illustrates GPC results that demonstrate cross-linking of PEG dialkene after reaction with ROS.
Figure 11:
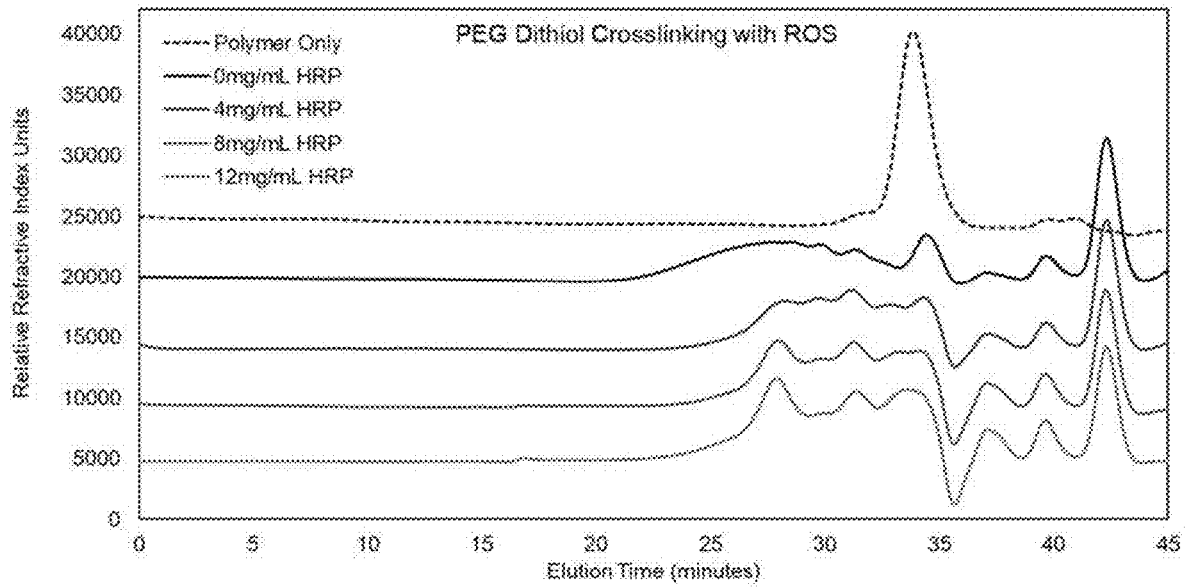
FIG. 11 illustrates GPC results that demonstrate cross-linking of PEG dithiol after reaction with ROS.
Figure 12:
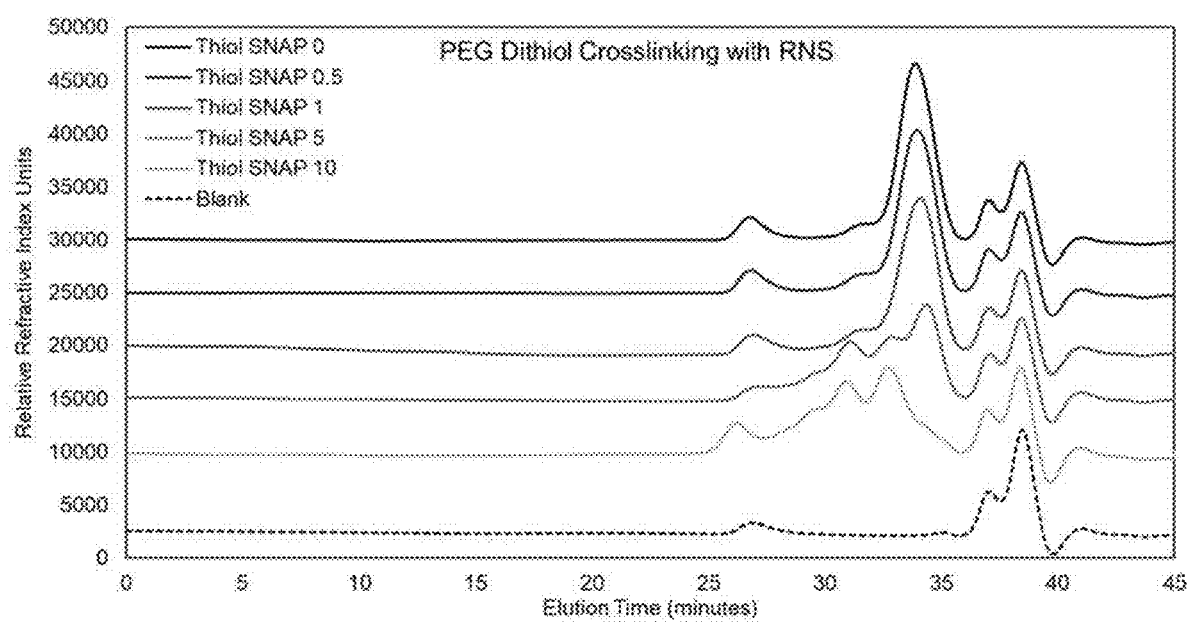
FIG. 12 illustrates GPC results that demonstrate cross-linking of PEG dithiol after reaction with RNS.

Diseases or injuries often lead to the production of an abnormal level of free radicals, which slow down the recovery process and may even cause secondary damages to cellular components. Described herein is a novel approach that enables the targeted delivery and sustained presentation of a therapeutic molecule to a site of disease or injury while also potentially decreasing the concentration of damaging free radicals. Importantly, the approach is versatile, as the compositions and geometries of the conjugate of the present invention can be mixed and matched to tune response, and the polymer component of the conjugate is easily functionalized with a wide range of bioactive factors.

While the following text may reference or exemplify specific components of a conjugate or a method of treating a disease or injury, it is not intended to limit the scope of the invention to such particular references or examples. Various modifications may be made by those skilled in the art, in view of practical and economic considerations, such as the size of a polymer component and the sequence of attaching an agent to the polymer backbone.

The articles "a" and "an" as used herein refers to "one or more" or "at least one," unless otherwise indicated. That is, reference to any element or component of the present invention by the indefinite article "a" or "an" does not exclude the possibility that more than one element or component is present.

The term "about" as used herein refers to the referenced numeric indication plus or minus 10% of that referenced numeric indication.

The term "alkyl" as used herein refers to saturated carbon or carbon chains, which can be linear or branched. C1-C4 alkyl includes a carbon chain that has 1, 2, 3, or 4 carbon.

"Alkenyl" and "alkynyl" include carbon chains containing at least one unsaturated C—C bond. Non-limiting examples of alkene or alkenyl includes ethylenyl, propenyl, and butenyl. The alkenyl and alkynyl can be substituted with one or more substituents in a functional group-containing moiety. Non-limiting examples of the substituents include alkyl, cycloalkyl, heterocyclyl, carbonyl, carboxylate, amide, ester, thiol, hydroxyl, cyano, aryl, and heteroaryl.

The term "pharmaceutical composition" refers to a mixture of a conjugate disclosed herein with other chemical components, such as diluents or additional carriers. The pharmaceutical composition facilitates administration of the conjugate to an organism. Multiple techniques of administering a pharmaceutical composition exist in the art including, but not limited to, oral, injection, aerosol, parenteral, and topical administration. In some embodiments, pharmaceutically acceptable salts of the conjugate can be included into the composition.

The term "subject" encompasses any animal, but preferably a mammal, e.g., human, non-human primate, a dog, a cat, a horse, a cow, or a rodent. More preferably, the subject is a human.

The term "therapeutically effective amount" refers to an amount of a compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The present invention finds application in the treatment of various diseases and injuries. Examples of the target disease or injury include traumatic brain injury, burn injury, inflammatory disease, bacterial infection, neurological disorder and ischemic disease. More examples of specific diseases include arthritis, vasculitis, lupus, Alzheimer's disease, Parkinson's disease, muscular dystrophy, cardiac diseases, and stroke. In addition, procedures or conditions such as organ transplantation, ulcers, and radiation also result in production of free radicals, which can be mitigated by the conjugate described herein.

The conjugate generally contains a polymer covalently linked to 1, 2, 3 or more moieties each containing a functional group. Suitable groups include alkyne, alkene, thiol, and other groups which crosslink upon reaction with free radicals. In some embodiments, the polymer and/or the one or more moieties of the conjugate comprise a degradable linkage. The degradation of the linkage promotes the clearance of the conjugate from the blood circulation or the release of a therapeutic agent or diagnostic agent. In some embodiment, a therapeutic agent or a diagnostic agent may also be incorporated to the polymer backbone or any other moieties (e.g. alkene or thiol containing moiety, or any other moiety attached to the polymer or the conjugate).

The functional group-containing moiety of the conjugate can serve as a substrate for the free radicals or stimuli to limit their effects on cells, while simultaneously crosslinking the polymer to decrease its diffusivity and effectively immobilize it at the site of high stimuli concentration (e.g. site of free radical generation). The concentration of the radicals will meanwhile be reduced as a result. Moreover, if the polymer or any structural moiety attached thereto is also functionalized with a therapeutic agent, the stimuli-mediated crosslinking will essentially serve to localize the drug treatment at the injury site by honing polymerization to the region where the stimuli concentration is highest. Furthermore, a sustained delivery of the therapeutic agent at the injury site can be achieved. Each of these aspects of the conjugate can improve outcome following an injury by limiting secondary insults caused by the stimuli and improving the delivery. Collectively, this novel, multi-potent approach will significantly enhance cell survival following an injury and facilitate healing process.

Various polymerizable moieties are suitable for the present invention. Non-limiting examples include acrylates, acrylamides, acrylonitrile, styrenes, dienes and vinyl monomers. Any of these alkenes can be optionally substituted. For example, a methyl substituted acrylate, (metha)acrylate is a preferred alkene that polymerizes readily upon exposure to free radicals. In addition, acrylates include various esters such as methyl, ethyl, propyl and butyl esters. Likewise, acrylamides may have one or more substituents on the amide nitrogen. A thiol group can also utilized for thiol-ene or thiol-thiol reaction initiated by free radicals to promote the intermolecular cross-linking of the conjugate.

Polymers of the conjugate can be natural or synthetic, linear or branched, or having a single arm or multiple arms. Non-limiting examples of synthetic polymer include polymeric polyol, poly(lactic acid) (PLLA), poly(lactic-co-glycolic acid) (PLGA), Poly(caprolactone), Poly(vinyl alcohol), Polyurethenes, Polyamides and Poly(2-hydroxyethyl methacrylate) (Poly(HEMA)). Natural polymer include, for example, Chitosan, Collagen, Gelatin, Hyaluronic Acid, Chondroitin Sulfates, Fibrin, Alginate, Agarose and Cellulose.

Polyethylene glycol (PEG) is a hydrophilic and biocompatible and highly customizable polymer used across a wide variety of medical applications. PEG is particularly attractive as a base polymer because it is easily functionalized with biological molecules including peptides and full-length proteins. PEG based hydrogels are commonly used for cell encapsulation, tissue engineering scaffolds, and drug delivery, frequently with chemical modifications tailoring them to specific tissue types and applications. PEGylation of drugs or other molecules is often used to increase the circulation time of the therapeutic and control its rate of clearance. One approach to rapidly polymerize individual PEG chains into a crosslinked hydrogel network with great control is to introduce acrylic ester (acrylate) groups to the end of PEG chains. These acrylate groups are readily crosslinked to each other, most often with the use of photoinitiators, which form radicals when exposed to white or UV light. For example, acrylated PEG can polymerize into a hydrogel network following exposure to the radicals generated by the photointiators. In fact, substantial research has focused on developing and identifying photointiators that minimize damage to cells and proteins from the compound itself, the UV light exposure, and the radicals that are generated, particularly for encapsulation. Cytotoxicity can still be significant, especially if too high a concentration of the photoinitiator is used. Importantly, research in photopolymerization has demonstrated that, when radicals are generated via a photoinitator in the presence of acrylated precursors (in this case methacrylated hyaluronic acid and methacrylated hyperbranched polyglycerol), cell damage is decreased compared to conditions where the precursors are absent. However, there has been report on the protection of cellular components using injury-related radicals to mediate polymerization.

As an example, PEG diacrylate (PEGDA) is a common configuration of acrylated PEG, and consists of a linear PEG chain flanked by terminal acrylate groups at each end. Multi-arm PEG acrylate configurations, which comprise PEG molecules with multiple branches of acrylate-capped PEG chains extending from a common core, are also commercially available. These multi-arm acrylated PEGs offer more reactive sites per molecule and may be more efficient as radical sinks. PEGs across a range of molecular weights (corresponding to an increasing PEG chain length) from 250 g/mol to 30,000 g/mol can be used for the conjugate of the present invention.

PEGs of multiple arms offer even more sites for the introduction of alkenes or therapeutic agents. PEGs of various configurations (e.g. block shape, star shape, comb shape and brush shape) may also impact the geometry of the ultimate polymer network. In some embodiments, the PEG is linear. In some embodiment, the PEG has 2, 3, 4, 5, 6, 7, 8 or more arms. Non-limiting examples of the molecular weight for the PEG range from about 250 to about 50,000 dalton, from about 250 to about 20,000 dalton, from about 250 to about 10,000 dalton, from about 250 to about 8,000 dalton, from about 250 to about 5,000 dalton, from about 250 to about 3,000 dalton, from about 250 to about 1,000 dalton, from about 500 to about 10,000 dalton, from about 50 to about 5,000 dalton, from about 1000 to about 10,000 dalton, and from about 1000 to about 50,000 dalton.

The conjugate of the invention is not limited to acrylate-containing PEGs. For example, acrylated or methacrylated polymers, including hyaluronic acid, gelatin, and collagen—all of which exploit the reactivity of the acrylate or methacrylate residues to increase the molecular weight of the polymer and/or crosslink the polymer network, can also be used in the present invention. Other acrylated or methacrylated molecules can be used, including chitosan, gelatin, hyaluronan, or even our own collagen methacrylamide. Also, other chemistries could be used that are amenable to radical-induced polymerization, such as thiol-ene, and thiol-thiol. Therefore, the polymerizable moiety of the conjugate can be any combination including alkene-alkene, thiol-ene, thiol-thiol, and methacrylate-methacrylate. The polymerization process may also involve polymer reversible addition fragment chain transfer (RAFT), atom transfer radical polymerization (ATRP), nitroxide mediated radical. By varying the functional group, the polymer and the geometry of the polymer, the reactivity of the conjugate may be controlled to limit the movement of the cross-linked polymer and localize its delivery of a therapeutic.

Targeted drug delivery offers the promise to selectively and precisely deliver drug payloads directly to the cells and tissues that require the therapeutic, which can minimize required dosages and off-target side effects. Successful targeted drug delivery requires a balance of specificity and sensitivity. An approach that does not target cells but rather a species (e.g. reactive oxygen species) that is produced under pathologic situations may allow for targeted delivery to be applied to a broader range of injury and disease conditions.

Native free radicals include hydroxyl (OH.), superoxide ($O_2.^-$), nitric oxide (NO.), and lipid peroxyl (lipid-OO.). Although not free radicals themselves, hydrogen peroxide ($H_2O_2$), peroxynitrate ($ONOO^-$), and other species are categorized as oxidants which can mediate free radical reactions or be decomposed into free radicals themselves. Low levels of free radicals are continuously present in vivo and play a crucial role in many cellular functions, such as combating infectious organisms and servicing as messengers in cell signaling cascades. A delicate steady state exists between formation of free radicals in vivo and their detoxification through natural antioxidant mechanisms. In injured and diseased tissues, the production of free radicals is often greatly increased, thereby overwhelming native antioxidant mechanisms and resulting in persistent elevated concentrations of free radicals in afflicted tissues and associated damage. The elevated production of free radicals in injured and diseased tissues are capable of inducing crosslinking of functional groups of the conjugate of the present invention. After initiation of crosslinking and immobilization of the conjugate, a drug payload can be delivered to the cells and tissues that require the treatment Accordingly, the conjugate may also contain a therapeutic agent or a diagnostic agent for the diagnosis, detection or treatment against a disease such as inflammatory diseases, neurological disorders, and bacterial infections.

Non-limiting examples of therapeutic agents include small molecule drugs, large molecule biologics, antibodies, antibody fragments, proteins, glycoproteins, DNA, RNA, PNA, metal complexes, enzymes, toxins and sugars. Further examples of the agent include: anti-inflammatory drugs (NSAIDS), neurotrophic factors (BDNF, CTNF, NGF, etc.), antibiotics and antimicorbial peptides, and angiogenic factors (Hemoglobin, VEGF, etc.).

Non-limiting examples of the diagnostic agents include contrasting agent, radiolabeled species (e.g. radionucleotide, radioisotope), reporters (e.g. phosphorescent agent, luminescent agent, fluorophore), protein, and metal complexes.

A combination of therapeutic agents can be incorporated into a conjugate. For example, a mixture of trophic factors or other neuroprotective molecules, such as anti-oxidants, or neuroregenerative molecules can be linked to the polymer. Non-limiting examples of antioxidants include superoxide dismutase, melatonin, nitroxides, and hydroxystilbene oxyresveratrol.

The therapeutic agent, diagnostic agent or targeting agent can be attached to a polymerizable functional group as described above or any moiety attached to a polymer backbone. When exposed to free radicals, the polymerizable functional group undergoes polymerization to form a polymer network of the agent. Suitable agents and polymerizable functional group are as those described herein. In some embodiments, a polymer backbone is not needed as the cross-linking process will generates a polymer network.

In some embodiments, the agent is attached to the polymer backbone of the conjugate. In some embodiments, the therapeutic agent, diagnostic agent or targeting agent is linked to the polymer backbone via a degradable linkage. After the formation of the polymer network, the degradation of the linkage releases the agent.

In some embodiments, the therapeutic agent is a trophic factor. Trophic factors allow a neuron to develop and maintain connections with its neighbors. These small proteins work through their receptors on the surface of the nerve cells.

In some embodiments, pure imaging applications, a fluorophore or light-emitting compound is the payload, which is attached to the polymer backbone. Immobilization of the conjugate in a desired region thus allows for imaging applications.

In some embodiments, the trophic factor is a brain derived neurotrophic factor (BDNF). BDNF is critical to neuronal survival and development and has been shown to be neuroprotective in models of TBI, preserving neuron viability against the effects of secondary injury. However, the therapeutic potential of soluble BDNF is limited because of difficulties in maintaining its concentration at necessary levels in the appropriate locations because of its limited capacity to cross the blood-brain barrier, its high diffusivity, and its rapid clearance when in soluble form. Focusing the delivery of BDNF with a biomaterial that targets an area via the concentration of free radicals can increase the local concentration of the therapeutic to improve its efficacy, and conjugating it to a biomaterial can delay its clearance in vivo.

Although BDNF has been shown to have beneficial therapeutic effects in multiple models, its utility is currently limited. Soluble BDNF is rapidly cleared in vivo and is unable to cross the blood-brain barrier at a therapeutically relevant rate. While biomaterial drug delivery therapies for sustained release of soluble BDNF are being investigated, current technologies are limited by non-uniform distribution profiles.

A mixture of acrylated PEG and acrylated PEG functionalized with therapeutic was introduced to the body following injury or disease. Free radicals at the injury site reacted with the acrylate groups to induce crosslinking, which immobilized the therapeutic at the site of highest radical concentration. PEG that was not polymerized or crosslinked was cleared. The accumulation of therapeutic-functionalized acrylated PEG is illustrated in FIG. 1. The conjugate of the present invention improves the efficacy of BDNF by immobilizing the trophic factor at the site of secondary injury. BDNF that is covalently coupled to a surrounding matrix would result in sustained presentation that would not be cleared until degradation of the carrier matrix.

While it is desirable to accumulate the polymer and payload at sites of free radical production, ultimately the polymer should be cleared. For conjugates containing a therapeutic agent or a targeting agent, it will be necessary in some cases for the agent to be released from the polymer to act therapeutically. Therefore, enzymatically and/or hydrolytically degradable sites can be introduced into the conjugate or the resulting polymer to facilitate degradation and payload release. In an exemplary embodiment, the therapeutic agent is an anti-cancer agent and the conjugate is immobilized at the site of a tumor. In some embodiments, the agent can be released from the polymer network after the cleavage of the linkage moiety. The polymer network can also be cleared from the subject due the cleavage of the linkage.

Accordingly, the conjugate may contain a linkage that is cleavable under in vivo conditions. As a result, the degradation, stability, clearance, payload delivery and other characteristics can be further controlled. The cleavable or degradable linkage can be installed in the polymer backbone, a structural moiety attached to the polymer backbone, or any functional group-containing moiety in the conjugate. Exemplary degradable bonds for the linkage include enzyme-sensitive peptide linker bonds, self-immolative linker bonds, acid and base-sensitive linker bonds, pH sensitive linker bonds, multifunctional organic linking agent bonds, multifunctional inorganic crosslinking agent bonds and peptidic backbone bonds. In some embodiments, the linkage is degradable by hydrolysis. Hydrolysis involves chain scission when water is added to the conjugate. Anhydrides, esters and amides are all susceptible to hydrolysis. For example, PEG can be functionalized with degradable ester linkages using lactide or glycolide segments.

In some embodiments, the conjugate contains an enzymatically cleavable linkage. These enzymatic cleavage sites can be used to allow degradation of the crosslinked polymer (e.g. PEGDA) and/or to introduce the ability to release to bound therapeutic molecule. In this fashion, the free radicals would localize the accumulation of the therapeutic, and the enzymes would release the therapeutic to act locally. This would be advantageous for molecules that must be internalized by cells. For example, the enzyme-specific sequence can be coupled on one end to the PEG/PEGDA and on the other end to the therapeutic molecule. The preparation of sequence-specific enzymatic degradation of peptides incorporated into hydrogels are well known in the art (e.g. Hubbell-West, J. L.; Hubbell, J. A. Macromolecules 1999, 32, 241-244). For example, matrix metalloproteinase (MMP) sensitive linkages can be readily introduced into hydrogels via Michael addition of cysteine-functionalized peptides across acrylates, maleimides and vinyl sulfones.

In some embodiments, the conjugate contain a photonically cleavable linkage. For example, photodegradation of hydrogels can be introduced by using an ortho-nitrobenzyl (o-NB) linker group.

The therapeutic potential of the conjugate can be fine-tuned by conjugating different alkenes into a polymer. Each of the alkenes may provide one or more functions including reduction of radicals, immobilization, and neuroprotection. Likewise, different therapeutic agents can be attached to a conjugate, and each of the agents is effective at radical reduction and/or neuroprotection.

Also provided herein is a mixture of conjugates, which display different configurations or functions. In some embodiments, one group of acrylated PEGs is effective at conferring neuroprotection, while another group of acrylated PEGs results in immobilization. In some embodiments, some of the conjugates in the mixture have a synthetic polymer backbone while some other conjugates in the mixture have a natural polymer backbone.

Another aspect of the invention provides a composition comprising a pharmaceutically acceptable carrier formulated for delivery to the site of a disease or injury characterized by the abnormal production of free radicals, and the conjugate or conjugate mixture of the present invention. The composition may contain one or more additional diluents or carriers.

Another aspect of the provides a system or a kit comprising a first conjugate and a second conjugate. The first conjugate comprises a linear or branched polymer covalently linked to one or more moieties each containing a polymerizable functional group, wherein a cross-linked polymer network is formed through intermolecular reactions or crosslinking between the functional groups after being exposed to an abnormal level of free radicals associated with a disease or injury. The scope and definition of the polymer and the functional group are as described above. In some embodiments, the first conjugate further contains one or more first cycloaddition functional groups, which are amenable to click chemistry. In some embodiments, the first conjugate does not contain a therapeutic agent.

The second conjugate comprises a linear or branched polymer covalently linked to one or more therapeutic or diagnostic agents, and one or more second cycloaddition functional groups. The scope of the polymer and the agents are as described above. The first and second cycloaddition functional groups are selected from dibenzocyclooctyl (DBCO), azide, trans-cyclooctene and tetrazine and complimentary to each other for click chemistry reaction. Complementary cycloaddition functional groups functional groups include DBCO—azide pair, and trans-cyclooctene—tetrazine pair.

Click chemistries are well-characterized bioorthogonal reactions that are highly efficient, selective, and proceed under mild conditions. The reactions occur rapidly and do not interfere with functionalized biomolecules or biochemical processes. Click chemistries are used to minimize non-specific cross reactivity and promote the covalent attachment of dissimilar molecules. Due to the unique advantages of bioorthogonal reactions, they have been employed successfully in drug discovery, bioconjugation, and radiotherapy applications. The alkyne-azide cycloaddition is one such reaction that fulfills the requirements of click chemistry, but it is catalyzed by the cytotoxic copper (I) enzyme. The reaction has been optimized for living systems by incorporating the alkyne into a strained cyclooctyne ring to increase its reactivity. Dibenzylcycloctyne (DBCO) is a common molecule containing the strained alkyne component for the click reaction with azide groups. Previously, the azide-DBCO system has been used for live imaging of azide-labeled components in humans and to enhance targeting to cancers. The new system has the potential for more effective in situ crosslinking, as polymers can easily be modified to contain the bioorthogonal chemistries.

Each of the first and second conjugates may also contain linkages for linking the polymerizable functional group and the cycloaddition functional group. In some embodiments, the linkages are degradable. The scope of the linkages are as described above.

The first conjugate, after being immobilized at a site of a disease or injury associated with excessive high amount of radicals, will couple to the second conjugate through click chemistry. The advantages of this two component system include greater reactivity (as reactive sites are no longer encumbered by therapeutics), improved flexibility with dosing, protection of therapeutic factors from harsh levels of free radicals, and the ability to pre target injured or diseased tissues. In some embodiments, the first and second conjugates are administered simultaneously. In some embodiments, the first and second conjugates are administered sequentially.

Another aspect of the invention provides a method of treating a disease or injury associated with an elevated level of free radicals. The disease or injury may include for example traumatic brain injury, burn injury, inflammatory disease, bacterial infection, neurological disorder and ischemic disease. The method is also applicable to procedures or conditions such as organ transplantation, ulcers, and radiation. The method includes administering to a subject in need a conjugate of the present invention or the first and second conjugates of the system/kit of the invention.

Besides protecting cells from radical-induced damages and alleviate oxidative stress, the conjugates or the pharmaceutical composition of the present invention can be immobilized at a site for targeting or treatment and serve as a vehicle to deliver a therapeutic or diagnostic agent.

Free radicals are species left with at least one unpaired electron, which renders them extremely reactive and capable of causing significant damage to proteins, lipid membranes, nucleic acids, and other critical cellular components. Native free radicals include hydroxyl (OH.), superoxide ($O_2.^-$), nitric oxide (NO.), and lipid peroxyl (lipid-OO.). Although not free radicals themselves, hydrogen peroxide ($H_2O_2$), peroxynitrate ($ONOO^-$), and other species are categorized as oxidants which can mediate free radical reactions or be decomposed into free radicals themselves. Low levels of free radicals are continuously present in vivo and play a crucial role in many cellular functions, such as combating infectious organisms and servicing as messengers in cell signaling cascades. A delicate steady state exists between formation of free radicals in vivo and their detoxification through natural antioxidant mechanisms. In injured and diseased tissues, the production of free radicals is often greatly increased, thereby overwhelming native antioxidant mechanisms and resulting in persistent elevated concentrations of free radicals in afflicted tissues and associated damage.

In an exemplary embodiment of treating burn injury when an abnormal amount of radicals is generated, application of acrylated PEG will effectively promote heating of the skin by reacting with the excess radicals to for cross-linked polymers. When acrylated-PEG is doped with fluorescent-PEG-acrylate, the fluorescent acrylated PEG will become trapped after cross-linking within excised tissues and fluorescent PEG will be visible in the sections. Fluorescence of the collected supernatants can be measured to assess how quickly the fluorescent PEG diffuses out of the excised tissues in the presence and the absence of radicals.

In an exemplary embodiment for delivering a diagnostic agent or a therapeutic agent to a site of disease that produces excessive free radicals (e.g. tumor), the subject is injected with acrylated PEG, which is allowed to circulate. Following administration of a fluorescent acrylated PEG, the subject can be imaged using in vivo optical imaging to visualize the distribution of acrylated PEG within the subject. By using a fluorescent antibody for specific epitopes on the tumor cells, it can be determined if the acrylated PEG and fluorescence from the tumor tags are co-localized. For a conjugate that can become immobilized within a diseased tissue or area it can also effectively deliver a therapeutic agent or transport a diagnostic agent to the tissue or area.

In some embodiments, the injury is a wound associated with a higher than normal level of free radicals near the wound site. In some embodiments, the conjugate further comprises a therapeutic agent. In some embodiments, the therapeutic agent is an anti-cancer agent and the conjugate is immobilized at the site of a tumor.

EXAMPLES

Example 1

Preparation and Testing of Acrylated PEGs.

First, the potential of acrylated PEG to react with different free radicals was assessed. One of the advantages of PEG as the platform biomaterial is the wide array of sizes and forms that are commercially available. For example, PEG diacrylate (PEGDA) is a common configuration of acrylated PEG, and consists of a linear PEG chain flanked by terminal acrylate groups at each end. Multi-arm PEG acrylate configurations, which comprise PEG molecules with multiple branches of acrylate-capped PEG chains extending from a common core, are also commercially available. These multi-arm acrylated PEGs offer more reactive sites per molecule and may be more efficient as radical sinks. The reactive potential of commercially available PEGDA across a range of molecular weights (corresponding to an increasing PEG chain length) from 250 g/mol to 10,000 g/mol was investigated. The experiment also screened 4-arm PEG acrylate, which offers more reactivity per mole, at 2 different molecular weights, 2,000 g/mol and 10,000 g/mol. Different concentrations of these acrylated PEG molecules were investigated between 0 uM and 5 mM based on preliminary results with 1,000 g/mol PEGDA and preliminary antioxidant studies in the literature.

The dose-response ability of the acrylated PEGs to react with a variety of free radicals generated with different methods and compounds can be characterized with the following assays.

DPPH Assay: To identify characteristics of acrylated PEG that best enhance their ability to convert free radicals, screening of various configurations of acrylated PEG was performed using the DPPH assay. DPPH is a stable radical with a characteristic absorbance of 517 nm, but upon reduction of DPPH, its signal at 517 nm greatly decreases. This assay has been used widely to investigate the radical scavenging potential of molecules. Briefly, DPPH dissolved in methanol was mixed with acrylated PEG solutions dissolved in phosphate buffered saline (PBS) at the specified concentrations. Acrylated PEG molecules reacted with DPPH for 30 minutes protected from light and then the absorbance of samples was read at 517 nm. Reductions in the absorbance of DPPH samples at 517 nm correspond to conversion of the DPPH to a non-reactive form.

ROS Assay: Generation of ROS was accomplished by combining hydrogen peroxide ($H_2O_2$) with horseradish peroxidase (HRP). Using this as a free radical source, the assay was run as a competition between a 3,3',5,5'-tetramethylbenzidine (TMB) substrate commonly used in ELISAs and the acrylated PEG sample conditions. A 50:50 mixture of H2O2 and TMB solution (BD OptEIA TMB Substrate Kit—Fisher Scientific) was combined with the sample condition being evaluated. Lastly, a solution of HRP at 0.1 µg/mL was added to initiate formation of ROS. The reaction was allowed to run for 60 seconds before a stop solution of 1M sulfuric acid was added to halt further progression of the assay. Absorbance was read at 450 nm and 540 nm on a Tecan Infinite M200 Pro. Background signal at 540 nm was subtracted from signal at 450 nm, per TMB substrate kit instructions.

S-nitroso-N-acetylpenicillamine (SNAP): To investigate the potential of acrylated PEGs to react with RNS, SNAP was used. SNAP is a NO. donor and been utilized previously to investigate the effects of NO. in vitro. The Griess method was used to quantify levels NO., which reveals the amount of nitrite that is produced. As NO. is produced, it is rapidly oxidized in the presence of oxygen to form nitrite. In the Griess method, sulphanilic acid is added to a solution containing nitrites. The nitrites react with the acid to form a diazonium salt, which forms a pink color when reacted with an azo dye agent (N-alpha-naphthyl-ethylenediamine) that can be read as a change in absorbance with a standard plate reader. Absorbance of reacted samples was read at 548 nm and the amount of nitrite present was quantified via comparison to the absorbance of a set of nitrite standards.

The reactivity of acrylated PEG with three different radical species—DPPH, ROS, and RNS—was evaluated with colorimetric assays. Preliminary characterization was performed with the DPPH assay, which is commonly used to evaluate the effectiveness of free radical scavengers. Increased levels of acrylated PEG substantially diminished the number of DPPH radicals present in solution by as much as 80%. Maximum reduction by acrylated PEG was 40% and 30% in ROS and RNS assays, respectively. In all three assays, increased levels of non-acrylated PEG had no effect on the concentration of free radicals present whereas increased amounts of acrylated PEG did reduce the level of radicals present in solution. This confirms that acrylate groups on the PEG chains are responsible for the reactivity with radicals. Although reactive with DPPH and ROS, in neither case did PEGDA reduce the radical concentration as well as ascorbic acid, a well-known, powerful antioxidant (Ascorbic acid controls were not able to be included with the RNS assay due to the strong pH sensitivity of the Greis Reaction) Thus, while the PEGDA may serve as a free radical scavenger, it will not be a primary anti-oxidant.

For all conditions, independent experiments were performed at least 3 times, and results compared with ANOVA. ED50 doses were identified for each PEG variant and each radical.

These studies provided a robust understanding of the reactivity of acrylated PEG with radicals relevant to the secondary injury cascade. The studies also allowed the identification of specific characteristics of acrylated PEG which best enhance their ability to scavenge these radicals. The reactivity of acrylated PEG molecules with radicals relevant to traumatic brain injury was likely commensurate with levels of protection offered by these compounds.

Second, the pretectioon conferred by acrylated PEG-mediated free radical consumption was evaluated. Rat dermal fibroblasts and rat cortical neurons were used as model cells. Cytotoxicity studies were completed by incubating these model cells with acrylated PEGs and protection studies were carried out by incubating the model cells with acrylated PEGS in the presence of hydrogen peroxide.

Rat Dermal Fibroblast Culture and Cellular Protection Studies (Cytotoxicity and Protection): Rat dermal fibroblasts (RDFs) that constitutively expressed green fluorescent protein (GFP) were isolated from a transgenic animal (a gift from the W.M. Keck Center for Collaborative Neuroscience). RDFs were cultured in DMEM containing 10% FBS, 1% L-glutamine, and 1% penicillin/streptomycin and seeded into 96 well plates at a density of 1500 cells/well. For cytotoxicity studies, acrylated PEG treatments were dissolved in fresh culture media, then added directly to RDF cultures and allowed to incubate for 24 hours. Cellular metabolic activity was then evaluated using the Vybrant MTT assay (Life Technologies) according to the manufacturer's instructions. For cellular protection studies, acrylated PEG treatments were added simultaneously with 600 µM H2O2 and allowed to incubate for 24 hours. Metabolic activity was again measured using the MTT assay.

Rat Cortical Neuron Culture and Cellular Protection Studies (Cytotoxicity and Protection): Rat cortical neurons were isolated from a timed pregnant animal at embryonic day 18 as described in the literature via techniques commonly employed in the literature. Neurons were cultured in Neurobasal media containing 2% B27 supplement, 1% KCl, 1% penicillin/streptomycin, and 0.5% L-glutamine and seeded into 96 well plates at a density of 100,000 cells/well. For cytotoxicity studies, acrylated PEG treatments were dissolved in fresh culture media without B-27 added, then added directly to cortical cultures and allowed to incubate for 24 hours. Cellular metabolic activity was then evaluated using the Vybrant MTT assay (Life Technologies) according to the manufacturer's instructions. For cellular protection studies, acrylated PEG treatments were added simultaneously with 20 µM H2O2 or 10 µM H2O2 and allowed to incubate for 24 hours. Metabolic activity was again measured using the MTT assay.

Cellular Metabolic Activity with MTT Assay: Cellular activity was measured following radical injury and subsequent acrylated PEG treatments using the MTT assay. (3-(4,5-dimethylthiazol-2-yl)-2,5-diphenyltetrazolium bromide) (MTT) was added to the cultures at 12 mM and allowed to incubate for 4 hours at 37° C. MTT was metabolized by mitochondrial activity to form an insoluble formazan product. The formazan product was solubilized by the addition of sodium dodecyl sulfate and further incubation for 4 hours. Absorbance measurements at 570 nm were collected to determine the amount of MTT that was metabolized by the culture and viability was reported as a percentage of MTT metabolized by uninjured control cultures.

In preliminary cytotoxicity studies, RDFs tolerated the presence of acrylated PEGs with greater than 88% activity in all conditions below concentrations of 1,000 µM. At concentrations greater than 1,000 µM, the toxicity in acrylated PEG conditions were mirrored that of ascorbic acid. Similarly, rat cortical neurons tolerated acrylated PEGs up to ~500 µM. Above 500 µM, decreases in cellular activity were observed, coincident with decreases observed in ascorbic acid conditions.

In addition to initiating crosslinking, the reaction of free radicals with acrylated PEGs may sequester or otherwise occupy the free radicals to prevent damage to nearby cells and offer a measure of cellular protection. Indeed, without acrylated PEG, exposure to H2O2 substantially reduced cellular metabolic activity of RDFs and cortical neurons. When even small concentrations of acrylated PEG was present, that injury was reduced. The positive influence of acrylated PEG was dose-dependent up to ~500 µM for RDFs and ~250 µM for cortical neurons. Decreasing viability at higher concentrations in protection studies occurred at slightly lower concentrations than in the cytotoxicity studies. We suspect that the additional oxidative stress induced by the H2O2 may have made the cells more susceptible to toxicity from the acrylated PEGs. This idea of acrylate conferred protection was also supported by the apparent protection of fluorophore discussed in the immobilization experiments. Ultimately, this ability of acrylated PEGs to confer additional protection may present the opportunity to ameliorate injured or diseased tissues through multiple independent mechanisms.

Third, the mobility of acrylated PEG treated with reactive species was evaluated. The formation of higher molecular weight species following exposure of acrylated PEG to free radicals and the effect on the mobility of the acrylated PEG were characterized.

Gel Permeation Chromatography (GPC): Radicals, especially those relevant to the secondary injury cascade were screened for their ability to induce acrylate-acrylate coupling to form higher molecular weight species of initial acrylated PEG chains. Samples of 20 mg/mL acrylated PEG of various molecular weight were reacted overnight in PBS with 0, 4, 8, or 12 mg/mL HRP in the presence of 80 µM H2O2 and 120 µM acetylacetone (ROS initiators) or 3 mM SNAP (RNS initiator). Following reaction, GPC samples were resuspended in 0.02% NaN3 in 0.5×PBS at 2 mg/mL and run through the column at 0.05 ml/min. Molecular weight for PEG species was estimated using an EasiVial PEG/PEO, pre-weighed calibration kit (Aligent Technologies). Peak height was used to calculate percent conversion and reported as the average of three experiments.

NMR Spectroscopy Measurements: Polymer samples for NMR were reacted overnight as described in GPC experiments. NMR samples were lyophilized and resuspended in deuterated chloroform. NMR spectra were obtained with a Bruker Avance III 600 MHz.

Acrylated PEG Immobilization Within Tissue Mimic: Immobilization models utilized collagen hydrogels as a tissue mimic. Type-I bovine collagen (Elastin Products Company) was reconstituted in 0.02N acetic acid at 3 mg/mL. Buffered hydrogel solutions were prepared using the following protocol for 1 ml: 20 µL HEPES, 130 µL 0.15N NaOH, 100 µL 10×PBS, 73 µL 1× PBS, and 677 µL collagen solution. Two radical sources were investigated. First, for ROS conditions, HRP was added to the buffered hydrogel solution. Hydrogel solutions were allowed to self-assemble at 37° C. for 2 hours. Acrylated PEG samples doped with 1% v/v 2,000 Da acrylate-PEG-rhodamine or acrylate-PEG-FITC (Creative PEG Works) were added to the hydrogels and allowed to diffuse throughout the gel overnight. H2O2 and acetyl acetone were added to the gels to initiate ROS formation and allowed to react for 24 hours. Second, for photoinitator conditions, 0.1 wt % Irgacure 2959 (BASF), a UV-sensitive photoinitiator, was included in the buffered hydrogel solution. Following hydrogel self-assembly and diffusion of PEG solutions, the hydrogels were exposed to UV light for 5 minutes to initiate formation of radicals from the photoinitiator. For both free radical types investigated, a series of 5 3-hour washes with PBS were performed after reaction with free radicals. The residual fluorescence of the hydrogels after all washes were measured (Rhodamine: excitation 540, emission 568; FITC: excitation 495, emission 525) using a Teacan Infinite M200 Pro Plate Reader.

Unreacted mono-acrylated PEG displayed strong signal from acrylate groups, as observed in the triplet at ~6 ppm. After reaction with ROS, the signal from that acrylate triplet is substantially reduced, indicating those acrylate groups have been consumed.

2,000 dalton PEG (2k PEG), 2,000 dalton monoacrylated PEG (2k PEG1A), and 2,000, 6,000, and 10,000 dalton PEGDA (2k PEGDA, 6k PEGDA, 10k PEGDA) were reacted with varying concentrations of HRP in the presence of H2O2 and acetylacetone. In the absence of ROS (0 mg/mL HRP), a single defined peak was observed which corresponded to the starting molecular weight of the polymer (2k PEG Mw: 1885, PDI:1.047; 2k PEG1A Mw:1813, PDI:1.053; 2k PEGDA Mw:1779, PDI:1.052; 6k PEGDA Mw:5843, PDI:1.024; 10k PEGDA Mw:10667, PDI:1.019). A peak at ~27 minutes elution time emerges and grows in intensity with increasing HRP concentration as can be seen in Figure GPC A and is present in all PEG sample curves. Analysis of this HRP peak via light scattering estimated the size of this species as ~53,000 daltons using a dn/dc value of 0.185. As HRP concentration increases the intensity of the initial polymer peak decreases. Additionally, the intensity of doublet peaks increases as can be observed in Figure GPC C, D, and E. Changes in peak height were utilized to calculate percent conversion of the polymer as displayed in Table 1.

To evaluate the potential for free radicals to crosslink the acrylated PEG sufficiently to immobilize it within a tissue, a collagen hydrogel model was used. Free radicals were introduced to the gels to initiate crosslinking and an acrylated-PEG fluorophore was included as an indicator to allow us to monitor the amount of polymer that remained within the hydrogels. Two free radical systems were used, Irgacure 2959, a photoinitiator to serve as proof of concept for our system, and the HRP-hydrogen peroxide system described earlier. Irgacure 2959 was developed as an efficient photoinitiator for a variety of materials science applications, whereas the ROS system was selected to expose the polymer to free radicals that may be commonly encountered in vivo. The number of radicals produced from Irgacure far exceeds those produced in the ROS conditions, which is expected to also increase acrylate-acrylate crosslinking events. An unintended consequence of this is the damaging effect of radicals on the fluorescence of the acrylate PEG rhodamine. Following exposure with UV, the fluorescence in non-acrylated PEG and PBS conditions was substantially decreased. However, in conditions where acrylate groups were present, very little decrease in fluroesence was observed indicating that the acrylate groups were able to protect rhodamine's fluorescence by intercepting radicals before they could damage the fluorophore. This speaks to the ability of acrylated PEGs to protect through free radical scavenging. Some fluorophore damage was observed in the ROS system, though to a much lesser degree than in the Irgacure experiments, again because the efficiency of Irgacure as a free radical initiatior far exceeds that of our ROS system. Because of these

TABLE 1

Percent conversion of polymer after reaction with ROS. Percent conversion was calculated by dividing peak height for each concentration of HRP by the peak height at 0 mg/mL HRP for each respective polymer and subtracting that from 1, with n = 3.
$[Conversion_{nHRP} = 1 - (PeakHeight_{nHRP}/PeakHeight_{0HRP})]$

| HRP Conc. | 2k PEG | 2k PEG1A | 2k PEGDA | 6k PEGDA | 10k PEGDA |
|---|---|---|---|---|---|
| 0 mg/mL | 0% | 0% | 0% | 0% | 0% |
| 4 mg/mL | 2.31% (±4.72) | 13.2% (±3.32) | 61.3% (±2.63) | 22.7% (±7.49) | 26.0% (±1.55) |
| 8 mg/mL | 0.486% (±5.37) | 30.9% (±3.71) | 61.9% (±6.33) | 32.3% (±3.17) | 30.0% (±3.11) |
| 12 mg/mL | 4.27% (±1.83) | 32.4% (±5.67) | 62.3% (±4.69) | 31.6% (±4.88) | 29.7% (±3.07) |

An increase in the molecular weight of acrylated PEGs was observed after reaction with ROS as determined by the emergence of higher molecular weight peaks in the elution spectrum after reaction with ROS. Additionally, there was a concomitant decrease in the intensity of the initial reactant peak, which indicates that the initial, low molecular weight polymer species were being converted into crosslinked, higher molecular weight species. Percent conversion was calculated from the change in this peak intensity. From the calculated percent conversion, it is clear that the percent conversion depends on the number of acrylates present, and the molecular weight of the staring polymer. The highest conversion was observed for 2,000 dalton molecular weight diacrylated PEG (~60%), even when low levels of HRP (and therefore radicals) were present. Diacrylated PEG at 6,000 and 10,000 daltons as well as monoacrylated PEG at 2,000 daltons showed lower conversion, with all sets topping out at approximately 30% conversion. Together these results suggest that smaller more mobile PEGs with more acrylate groups are able to react with free radicals more quickly, resulting in more crosslinking events than larger acrylated PEGs. Together, these results demonstrate that native ROS are capable of crosslinking acrylated PEGs.

differential effects of radicals, raw fluorescence was reported in figure IMMOBILIZATION at wash 0 (before washes, but after radical exposure) and wash 5 (after all washes were completed).

After reaction with radicals, hydrogel conditions containing acrylated PEGs retained higher levels of fluorescence than PBS or non-acrylated PEG conditions following all washes. This suggests that that acrylated PEG has become crosslinked within the hydrogel, making it more difficult for the polymer chains to diffuse out of the gel. Sufficient crosslinking will lead to the polymers becoming immobilized within the fibrillar collagen network, crosslinking to form an interpenetrating network trapped within the collagen fibrils. Fluorescence intensity was lower in conditions with non-acrylated PEG or PBS only. Further there was a molecular weight dependence in the residual fluorescence: higher molecular weight acrylated PEGs demonstrated a higher residual fluorescence. In the both ROS and Irgacure conditions, much of the 10k PEGDA was immobilized within the hydrogel, while less of the 6k PEGDA was immobilized within the gel, but little to none of the 2k PEGDA. This result demonstrates the dependence of the entrapment on the initial size of the polymer chain. As PEGDA molecules crosslink to one another, the molecular weight of the chains grows. For 2k PEGDA, each crosslinking event increases the molecular weight by 2,000 daltons. For 10k PEGDA, each crosslinking event increases the molecular weight by 10,000 daltons. Thus, 10k PEGDA conditions will reach an "immobilization threshold" after fewer crosslinking events than the 2k PEGDA. In the case of the ROS conditions where there are fewer radicals than irgacure, there was insufficient crosslinking to immobilize 2k PEGDA within the hydrogels. However, in GPC experiments, it was shown that the smaller molecular weight PEGDA had the highest conversion, presumably because the smaller chains were more mobile in solution and could interact with a greater number of radicals before the radicals extinguished. Moving forward, these results suggest a combination of sizes will be most optimal to achieve immobilization of a polymer network within a tissue: small, fast reacting acrylated chains that will undergo several cross-linking events, and larger chains that will amplify the size increase upon crosslinking.

Different PEG variants demonstrate different potential to decrease mobility based on size and number of reactive acrylates. Mixing and matching the PEGs achieved the objectives of immobilizing the fluorescent PEG and reducing radicals as well protecting the cells.

Investigation of Alternate Functional Groups: In addition to variation of polymer size and number of functional groups, examination of alternate functional chemistries was performed including thiol-thiol, alkene-alkene, and thiol-ene.

Reactivity of these alternate function groups was carried out with DPPH, ROS and SNAP assays. DPPH results showed that thiol-thiol chemistry reduced DPPH radicals most effectively. Similarly thiol-thiol coupling was observed to be the most effective in reducing ROS, meeting the threshold set by ascorbic acid, a known, powerful antioxidant. Alkene-Alkene coupling met the scavenging threshold set by acrylate-acrylate coupling in the ROS experiments.

Thiol and alkene functionalized PEGs were further characterized by GPC analysis. As the amount of HRP was increased, the amount of ROS increased. PEG dialkene demonstrated a coincident decrease in peak intensity of the initial 2k PEG dialkene peak and an increase in peak intensity of higher molecular weight species. PEG dithiol showed that even when HRP was not present, low levels of ROS resulting from the presence of hydrogen peroxide were able to crosslink the thiolated PEG as can be observed when comparing the 0 mg/mL HRP curve to the polymer only curve. This suggests that thiols functionalized to PEG are much more reactive with free radicals than either acrylates or alkenes. These carrying levels of reactivity offer an additional opportunity to vary parameters and specifically tune the reactivity of the conjugate to specific injury or disease states.

Thiolated PEGs were also evaluated with GPC after reaction with RNS. While acrylate functionalized PEGs did not exhibit crosslinking after reaction with RNS, thiol functionalized PEGs demonstrated the characteristic decrease in peak intensity of the initial 2k PEG dithiol peak and an increase in peak intensity of higher molecular weight species as more RNS (by increasing SNAP concentration) were added to the solution.

It will be understood by those of skill in the art that numerous and various modifications can be made without departing from the spirit of the present invention. Therefore, it should be understood that the various embodiments of the present invention described herein are illustrative only and not intended to limit the scope of the present invention.

The invention claimed is:

1. A biocompatible functionalized conjugate biomaterial for treating a disease or an injury characterized by the elevated production of free radicals, wherein the biomaterial comprises a plurality of linear or multi-arm polymers covalently linked to one or more moieties each containing a cross-linking functional group, wherein each cross-linking functional group consists essentially of an optionally substituted reactive alkene addition reaction functional group, wherein the reactive alkene functional groups form a cross-linked polymer network through intermolecular reactions between the reactive alkene addition reaction functional groups after being exposed in vivo to an elevated level of free radicals associated with the disease or injury, wherein the polymers comprise a first polyethylene glycol (PEG) and a second PEG, and the first PEG has smaller molecular weight than the second PEG and undergoes more intermolecular cross-linking between the reactive alkene addition reaction functional groups than the second PEG, wherein the polymers are optionally covalently linked to at least one therapeutic agent or at least one diagnostic agent, and wherein the difference in molecular weight between the first PEG and the second PEG ranges from about 4000 to about 8000 dalton.

2. The functionalized conjugate biomaterial of claim 1, wherein the alkene addition reaction functional group in each instance is independently substituted with a substituent selected from the group consisting of alkyl, cycloalkyl, heterocyclyl, aryl, and heteroaryl.

3. The functionalized conjugate biomaterial of claim 1, wherein the one or more moieties are each independently selected from the group consisting of acrylate, acrylamide, (metha)acrylate, (metha) acrylamide, and acrylonitrile.

4. The functionalized conjugate biomaterial of claim 1, wherein one or more moieties are each independently acrylate or (metha)acrylate.

5. The functionalized conjugate biomaterial of claim 1, wherein the therapeutic agent is selected from the group consisting of neurotrophic factors, anti-inflammatory drugs, antibiotics and antimicrobial peptides and angiogenic factors.

6. The functionalized conjugate biomaterial of claim 1, wherein the therapeutic agent is a neurotrophic factor selected from Brain-derived neurotrophic factor (BDNF), Ciliary neurotrophic factor (CNTF), Nerve growth factor (NGF), Glial cell-derived neurotrophic factor (GDNF) and Glia maturation factor (GMF).

7. The functionalized conjugate biomaterial of claim 1, further comprising a degradable linkage selected from the group consisting of a hydrolytically degradable linkage, an enzymatically degradable linkage, and a photonically degradable linkage.

8. The functionalized conjugate biomaterial of claim 7, wherein the degradable linkage links the therapeutic agent to the conjugate.

9. The functionalized conjugate biomaterial of claim 7, wherein the clearance of the polymer network is initiated by the degrading of the degradable linkage.

10. The functionalized conjugate biomaterial of claim 7, wherein the degradable linkage contains a group selected from the group consisting of an ester, an amide, a hydrazone, a carbamate, a disulfide, an oxime, a semicarbazide, a carbodiimide, an acid labile group, photolabile group, peptidase labile group and esterase labile group.

11. The functionalized conjugate biomaterial of claim 1, wherein the polymer has a molecular weight ranging from about 5,000 Dalton to about 30,000 Dalton.

12. The functionalized conjugate biomaterial of claim 1, wherein the first PEG and the second PEG differ by about 4000 dalton in molecular weight.

13. The functionalized conjugate biomaterial of claim 1, wherein the first PEG and the second PEG differ by about 8000 dalton in molecular weight.

14. The functionalized conjugate biomaterial of claim 1, wherein the first PEG has molecular weight ranging from about 250 to about 5,000 dalton.

15. The functionalized conjugate biomaterial of claim 14, wherein the second PEG has molecular weight ranging from about 6000 dalton to about 50,000.

16. The functionalized conjugate biomaterial of claim 14, wherein the second PEG has molecular weight ranging from about 10,000 dalton to about 50,000.

17. The functionalized conjugate biomaterial of claim 1, wherein the first PEG has molecular weight of about 2000 dalton, and the second PEG has molecular weight of about 10,000.

18. A pharmaceutical composition comprising the biocompatible functionalized conjugate biomaterial of claim 1 and a pharmaceutically acceptable carrier.

19. The pharmaceutical composition of claim 18, comprising a plurality of conjugates characterized by both natural and synthetic polymers.

20. A method of treating a disease or an injury characterized by an abnormal production of free radicals, comprising administering to a subject in need a therapeutically effective amount of a plurality of biocompatible functionalized conjugate biomaterial of claim 1, wherein a plurality of the conjugates form a cross-linked polymer network through intermolecular reactions between the functional groups after being exposed to an abnormal level of free radicals associated with the disease or injury.

21. The method of claim 20, wherein at least one of the polymer and the one or more moieties comprise a degradable linkage.

22. The method of claim 20, wherein the polymer is linked to a therapeutic agent or a diagnostic agent.

23. The method of claim 21, the functional group is selected from the group consisting of alkyne, thiol and alkene.

* * * * *